United States Patent
Reddy et al.

(10) Patent No.: US 7,229,763 B2
(45) Date of Patent: Jun. 12, 2007

(54) ASSAY SYSTEM USING LABELED OLIGONUCLEOTIDES

(75) Inventors: M. Parameswara Reddy, Brea, CA (US); Daniel A. Keys, Irvine, CA (US); Firdous Farooqui, Brea, CA (US)

(73) Assignee: Beckman Coulter, Inc., Fullerton, CA (US)

(*) Notice: Subject to any disclaimer, the term of this patent is extended or adjusted under 35 U.S.C. 154(b) by 244 days.

(21) Appl. No.: 10/408,626

(22) Filed: Apr. 7, 2003

(65) Prior Publication Data

US 2004/0219526 A1 Nov. 4, 2004

(51) Int. Cl.
- *C12Q 1/68* (2006.01)
- *G01N 33/53* (2006.01)
- *C12P 19/34* (2006.01)
- *C07H 21/04* (2006.01)
- *A61K 39/395* (2006.01)

(52) U.S. Cl. ............. 435/6; 435/7.1; 435/91.1; 536/24.3; 424/130.1

(58) Field of Classification Search ......... 435/6, 435/7.1, 91.1, 183; 436/94; 536/23.1, 24.3, 536/25.3; 530/387.1; 424/130.1
See application file for complete search history.

(56) References Cited

U.S. PATENT DOCUMENTS

| | | | |
|---|---|---|---|
| 4,385,126 A | 5/1983 | Chen et al. | |
| 5,635,352 A * | 6/1997 | Urdea et al. | 435/6 |
| 5,648,213 A | 7/1997 | Reddy et al. | |
| 5,789,165 A | 8/1998 | Oku et al. | |
| 5,807,755 A | 9/1998 | Ekins | |
| 5,955,268 A | 9/1999 | Granados et al. | 435/6 |
| 6,037,124 A | 3/2000 | Matson | 435/6 |
| 6,316,186 B1 | 11/2001 | Ekins | |
| 6,593,091 B2 * | 7/2003 | Keys et al. | 435/6 |
| 2002/0146745 A1 | 10/2002 | Natan et al. | 435/7.1 |
| 2003/0198967 A1 | 10/2003 | Matson et al. | 435/6 |

OTHER PUBLICATIONS

Page 136 in Webster's II New Riverside University Dictionary.*

* cited by examiner

*Primary Examiner*—Frank Lu
(74) *Attorney, Agent, or Firm*—Sheldon Mak Rose & Anderson

(57) ABSTRACT

The present invention provides a useful system for assays that comprises a solid support, a plurality of capture oligonucleotides immobilized onto the solid support, and complementary oligonucleotides attached to capture ligands. A detectable label can be directly attached to the capture oligonucleotides or the complementary oligonucleotides. The labeled oligonucleotides can be detected, and used to determine the quality of the assay. A labeled detector ligand corresponding to a target ligand can also be independently detected apart from the labeled oligonucleotide.

38 Claims, 7 Drawing Sheets

ASSAY SYSTEM USING LABELED OLIGONUCLEOTIDES

BACKGROUND

The following description provides a summary of information relevant to the present invention and is not a concession that any of the information provided or publications referenced herein is prior art to the presently claimed invention.

An assay can be performed in a number of ways such as the well-known sandwich technique and competitive technique. A variety of specific biological binding molecules can be labeled with a radioactive element, a fluorophore or a constituent which enters into an enzyme reaction. Thus a sample containing suspected target ligands can be analyzed, and the target ligand or target ligands can be detected quantitatively by forming a complex with a labeled anti-ligand, labeled as indicated above, and measuring the labeled constituent in the complex to determine the quantity of the target ligand. The anti-ligand binds to at least one site on the ligand to form a complex. "Ligand or target ligand" and "anti-ligand," as these terms are used herein, refer to antigens, antibodies, binding proteins, haptens, hormone receptors, and other biological molecules that can form a complex. The labeled anti-ligand used to detect and measure the target ligand in the complex is referred to herein as the "detector ligand."

In the sandwich technique mentioned above, a target ligand, a detector ligand, and a capture ligand are used in the assay. The detector ligand is detected quantitatively in a detector ligand/target ligand complex to determine a quantity of the target ligand present. The capture ligand in this technique is an anti-ligand that binds to the target ligand. The capture ligand and detector ligand typically bind to different sites on the target ligand so that there is no interference between the binding of the detector ligand to the target ligand and the capture ligand to the target ligand.

In the sandwich technique, the target ligand binds to the capture ligand to form a first complex. The detector ligand also binds to the target ligand in the complex to form a second complex in the sandwich, and the labeled constituent in the sandwiched ligands is detected quantitatively to deduce the quantity of target ligand present. Detection can be performed by: measuring radioactivity where the detector ligand is radioactive; measuring fluorescent light where there is a fluorescent label on the detector ligand; or spectrophotometrically where an optical density or wavelength change occurs through an enzyme reaction, or through fluorescent quenching. Detection may require separation of the sandwiched ligands from unbound ligands and this is generally done by separating the capture ligand attached or immobilized onto a surface from a solution containing unbound detector ligands.

The quantity of target ligand is deduced from the quantity of detector ligand detected, because the two quantities are generally directly proportional to each other in the sandwich technique. Parallel tests against known standards are employed for calibration.

The quantity of target ligand can be determined as an inverse proportion using the competitive technique previously mentioned above. With this technique, the capture ligand is contacted either simultaneously or sequentially with a target ligand and a known, limiting quantity of detector ligand. When the target ligand and detector ligand bind to the capture ligand, the quantity of detector-ligand detected in a binary complex with the capture ligand is inversely proportional to the amount of target ligand present. In this technique, the target ligand and detector ligand bind to the same site or sites in close proximity to each other to create competition.

The two techniques discussed above may be represented as follows where C designates the capture ligand, T represents the target ligand, and D represents the detector ligand.

| Sandwich | Competitive |
|---|---|
| 1. C + T → CT | 1. C + T → CT + C sequential |
| 2. CT + D → CTD | 2. (CT + C) + D → CT + CD |
| | 1. C + T + D → CD + CT simultaneous |

In addition to the sandwich and competitive assays described above, a variety of other techniques for assays are known, and include the following assays.

A method of using two different ligands tagged with two different tagging constituents in an immunoassay to independently detect and measure bound target ligand and bound receptor or capture ligand is described in U.S. Pat. No. 4,385,126 to James H. Chen et al.

A method of using oligonucleotides as capture agents for capture ligands in assays is described in U.S. Pat. No. 5,648,213 to Reddy et al.

Assay reagents and kits using oligonucleotides as capture agents in an assay array is described in U.S. Pat. No. 5,789,165 to Oku et al.

Although these systems are useful, there is always a need for systems with improved accuracy and lower costs. Accordingly, a need exists for a system that: offers greater precision in detection and quantification of capture ligands; offers greater precision in detection and quantification of target ligands; decreases variation arising from imprecision in the addition of reagents; offers correction for the variation arising from various assay manipulations; decreases the amount of binding interference caused by random attachment or positioning of a label on capture ligands; decreases the variability between different preparations of the same labeled capture ligands; provides reusable components to decrease expense in doing multiple assays; provides easy quality control and standardization methods; and can be provided as an assay kit.

SUMMARY

The present invention satisfies that need. The present invention provides a system that uses labeled oligonucleotides in assays to provide quality control, standardization, and greater precision in detection.

An assay device according to the present invention comprises a solid support and a plurality of capture oligonucleotides, wherein at least a portion of the capture oligonucleotides have detectable labels directly attached thereto immobilized onto the solid support.

An assay kit according to the present invention comprises a solid support; a plurality of capture oligonucleotides immobilized onto the solid support; and a plurality of capture ligands attached to complementary oligonucleotides, wherein at least a portion of the complementary oligonucleotides have detectable labels directly attached thereto. The complementary oligonucleotides in this assay device being capable of hybridizing under appropriate conditions to form double stranded nucleic acid duplexes with the capture oligonucleotides.

A sandwich assay method for a target ligand according to the present invention includes the step of providing a solid support having a plurality of capture oligonucleotides immobilized on the solid support. Another step is adding to the solid support a plurality of capture ligands attached to complementary oligonucleotides, wherein at least a portion of the complementary oligonucleotides have detectable labels directly attached thereto. Another step is providing conditions suitable for hybridization of the complementary oligonucleotides and the capture oligonucleotides to form double stranded nucleic acid duplexes. Another step is bringing the target ligand in contact with the solid support. Another step is adding a plurality of detector ligands having second detectable labels to the solid support. Another step is detecting the first detectable labels, thereby determining the amount of immobilized capture oligonucleotide. Another step is detecting the second detectable labels, thereby determining the amount of the target ligand.

Another sandwich assay method for a target ligand according to the present invention includes the step of providing a solid support having a plurality of capture oligonucleotides immobilized on the solid support, wherein at least a portion of the capture oligonucleotides have detectable labels directly attached thereto. Another step is adding to the solid support a plurality of capture ligands attached to complementary oligonucleotides. Another step is providing conditions suitable for hybridization of the complementary oligonucleotides and the capture oligonucleotides to form double stranded nucleic acid duplexes. Another step is bringing the target ligand in contact with the solid support. Another step is adding a plurality of detector ligands having second detectable labels to the solid support. Another step is detecting the first detectable labels, thereby determining the amount of immobilized capture oligonucleotide. Another step is detecting the second detectable labels, thereby determining the amount of the target ligand.

A competitive assay method for a target ligand according to the present invention includes the step of providing a solid support having a plurality of capture oligonucleotides immobilized on the solid support. Another step is adding to the solid support a plurality of captures ligands attached to complementary oligonucleotides, wherein at least a portion of the complementary oligonucleotides have first detectable labels directly attached thereto. Another step is providing conditions suitable for hybridization of the complementary oligonucleotides and the capture oligonucleotides to form double stranded nucleic acid duplexes. Another step is adding the target ligand to the solid support, wherein the target ligand competes with the detector ligand in binding to the capture ligand. Another step is adding a plurality of detector ligands having second detectable labels to the solid support. Another step is detecting the first detectable labels, thereby determining the amount of immobilized capture oligonucleotide. Another step is detecting the second detectable labels, thereby determining the amount of the target ligand.

Another competitive assay method for a target ligand according to the present invention includes the step of providing a solid support having a plurality of capture oligonucleotides immobilized on the solid support, wherein at least a portion of the capture oligonucleotides have first detectable labels directly attached thereto. Another step is adding to the solid support, a plurality of capture ligands attached to complementary oligonucleotides. Another step is providing conditions suitable for hybridization of the complementary oligonucleotides and the capture oligonucleotides to form double stranded nucleic acid duplexes. Another step is adding the target ligand onto the solid support, wherein the target ligand competes with the detector ligand in binding to the capture ligand. Another step is adding a plurality of detector ligands having second detectable labels onto the solid support. Another step is detecting the first detectable labels, thereby determining the amount of immobilized capture oligonucleotide. Another step is detecting the second detectable labels, thereby determining the amount of the target ligand In a preferred embodiment of the assay methods (i.e. sandwich and competitive assays), the first and second detectable labels are fluorophores that use the same excitation light source wavelength. The fluorophores typically have different emission wavelengths. The operator of the assay can use the same excitation light source, and determine the quality of the assay's capture components, labeled oligonucleotides immobilized on the solid support, and the concentration of the target ligand, by independently measuring the emission wavelength of each fluorophore.

In a preferred embodiment of the assay methods (i.e. sandwich and competitive assays), the steps of detecting the first detectable labels and detecting the second detectable labels are simultaneous.

DRAWINGS

These features, aspects and advantages of the present invention will become better understood with regard to the following description, appended claims and accompanying figures where:

Figure 5:
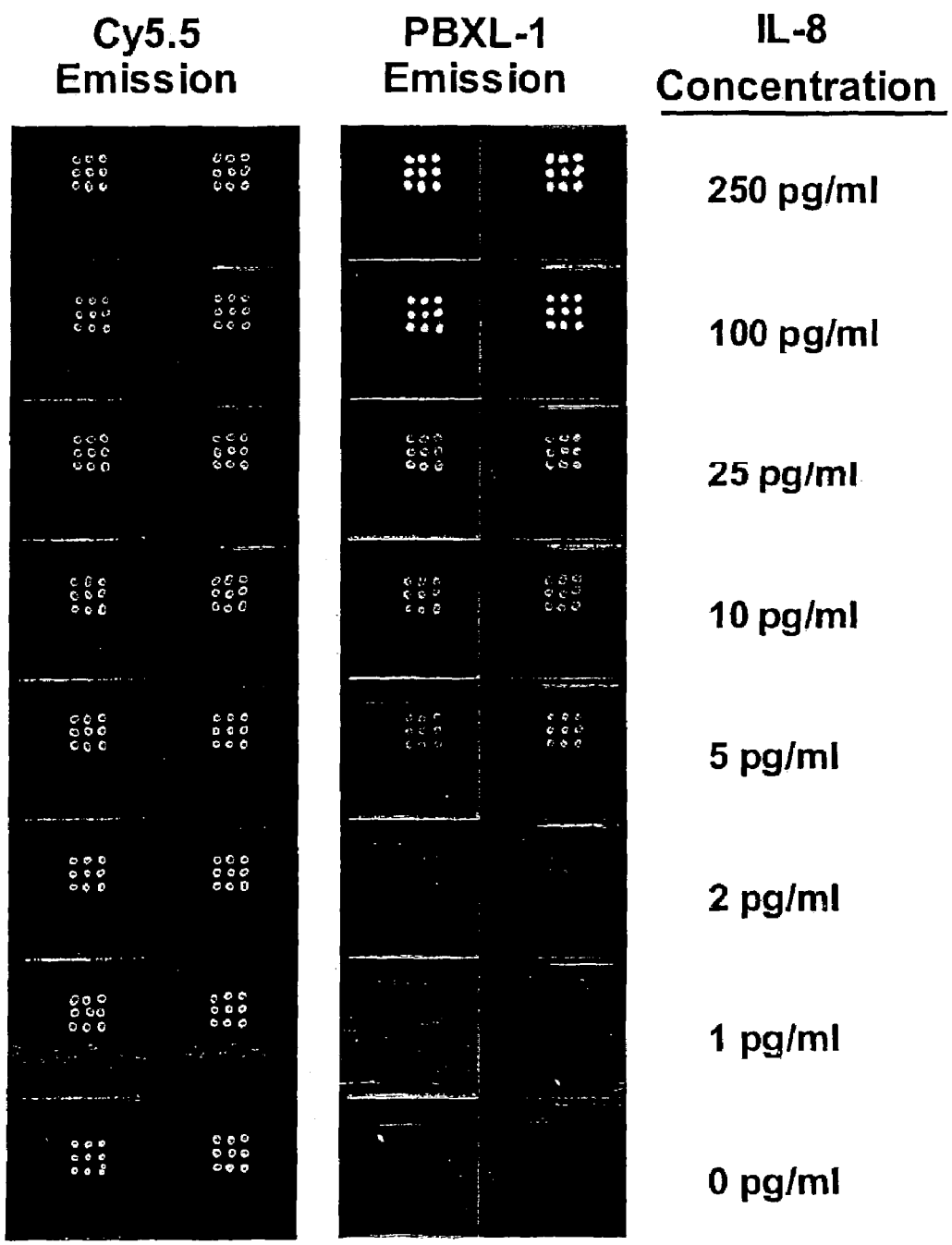

FIG. 5 shows label detection in a sandwich assay using IL-8 antigen as the target ligand with the invention where a CCD camera picture detects and illuminates the fluorescent label Cy5.5 directly attached to capture oligonucleotides immobilized onto a microtiter plate, as shown on the left side of the figure, and concentrations of fluorescent label PBXL-1 in bound IL-8 detector antibodies, as shown on the right side.

Figure 6:
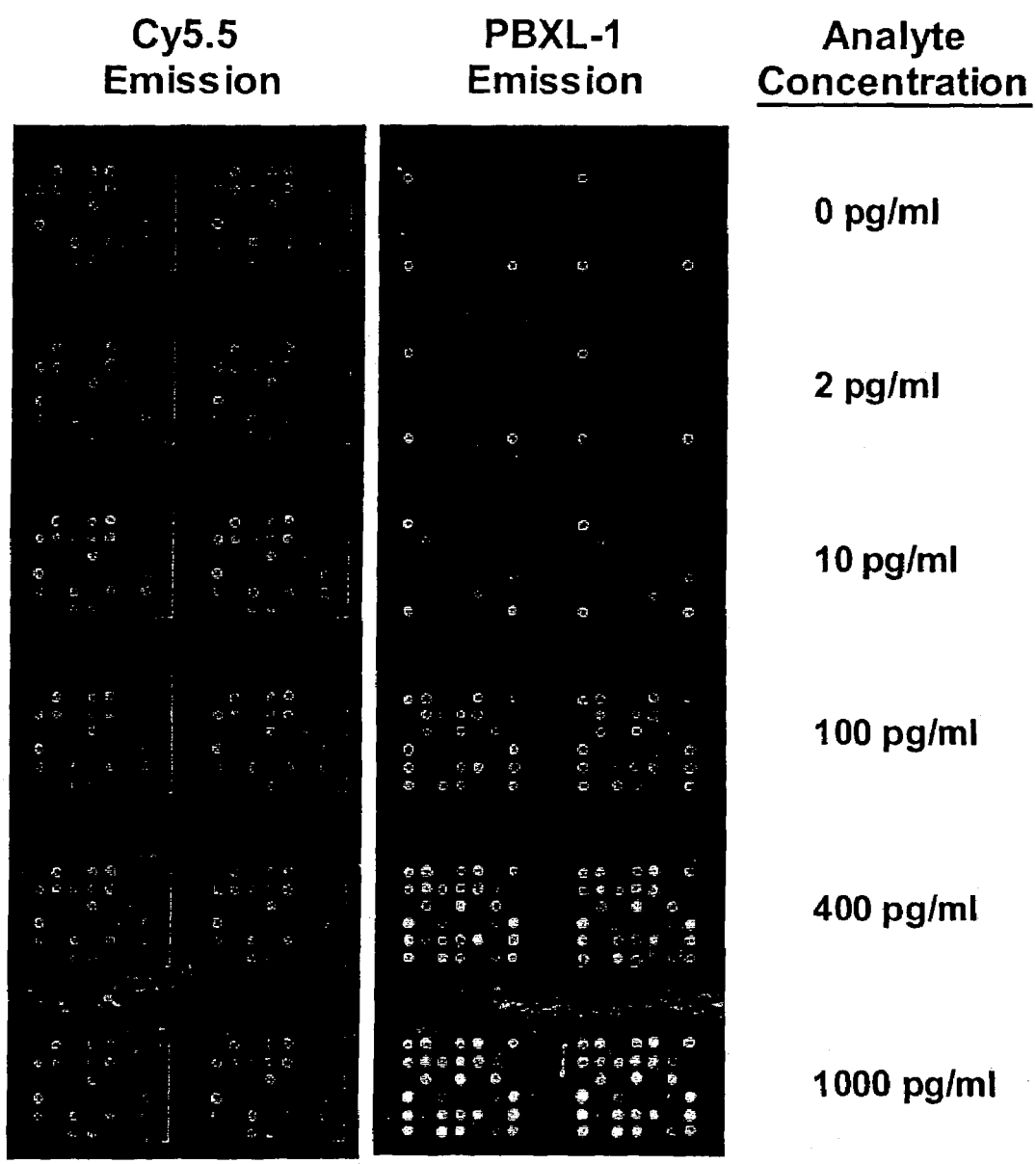

FIG. 6 shows label detection in a sandwich assay using the invention where a CCD camera picture detects and illuminates the fluorescent label Cy5.5 directly attached to complementary oligonucleotides attached to antibodies, as shown on the left side of the figure, and concentrations of fluorescent label PBXL-1 in bound detector antibodies for IL-2, IL-8, IL-12, Interferon-gamma, FGF-basic, and GMCSF antigens, as shown on the right side.

Figure 7:
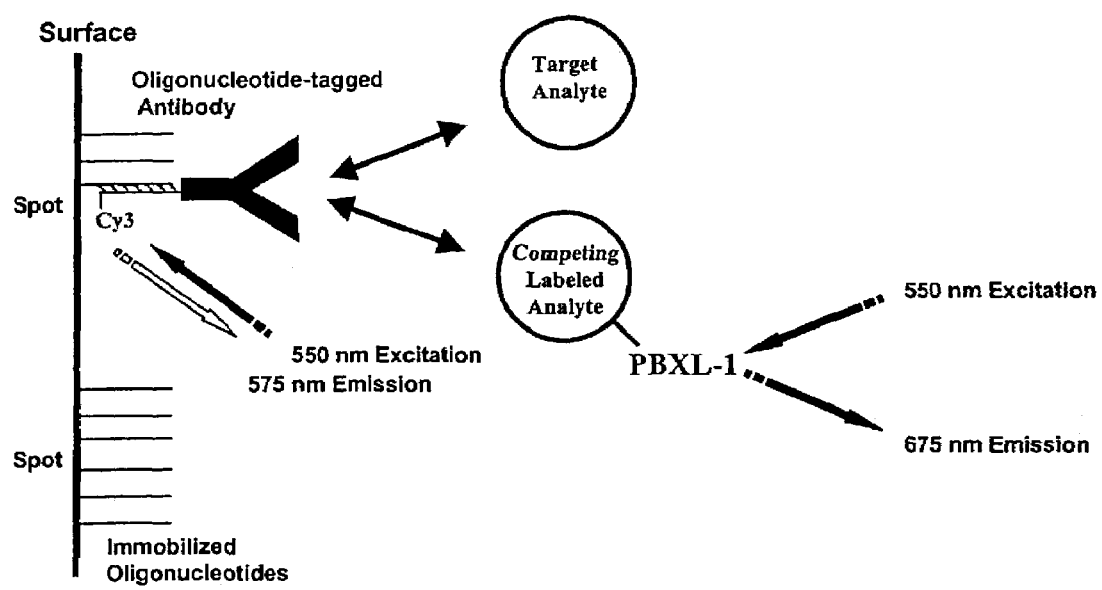

FIG. 7 depicts a competitive assay of the invention using immobilized complementary oligonucleotides; a Cy3 labeled oligonucleotide-tagged antibody, wherein the oligonucleotide is complementary to the capture oligonucleotide; a target analyte; and a competing PBXL-1 labeled analyte.

DESCRIPTION

The following discussion describes embodiments of the invention and several variations of these embodiments. This discussion should not be construed, however, as limiting the invention to these particular embodiments. Practitioners skilled in the art will recognize numerous other embodiments as well.

The present invention provides a system that uses capture oligonucleotides in assays to provide quality control, standardization, and greater precision in detection of target ligands. The use of capture oligonucleotides also yields efficient and easy manufacturing, and quality control methods that far exceed prior systems in ease of use for manufacturer and consumer.

As used herein, the phrase "directly attached" or "directly attaching" in referring to attaching a label to a capture or complementary oligonucleotide means that the label is attached to the oligonucleotide, and not to a ligand or anti-ligand which can also be attached to the oligonucleotide.

As used herein, the term "capture oligonucleotide" means an oligonucleotide immobilized or attached to a solid support which can bind a complementary oligonucleotide attached to a capture ligand.

As used herein, the terms "complementary oligonucleotide" or "oligonucleotide complementary to a capture oligonucleotide" refers to a nucleotide sequence attached to a capture ligand that hybridizes to the capture oligonucleotide under conditions suitable for hybridization thereby forming double stranded nucleic acid duplexes.

The present invention's use of detectable labels directly attached to capture oligonucleotides or to complementary oligonucleotides provides important innovations not taught in any of the references discussed in the background section.

The invention's use of labeled oligonucleotides is significant. In the invention, the label is directly attached to the capture oligonucleotide or the complementary oligonucleotide, and can be easily detected by a manufacturer or customer without the need or presence of a capture ligand. This provides an effective method of determining the quality of the assay device. In addition, oligonucleotide arrays are more stable than the antibody arrays that can be used as a labeled capture ligand, and oligonucleotides have a longer shelf life. Therefore, a user of the present invention can have a readily available labeled oligonucleotide assay device on the shelf, and an easily verifiable quality control system in place.

Another benefit of the present invention is that the proximity and orientation of labels on an oligonucleotide can be more easily and precisely controlled. For example, using directly attached labels on oligonucleotides in the invention bound to a surface, the distance and orientation (and therefore the interaction) of a fluorescent dye to the surface is uniform, and can be easily controlled, resulting in more uniform and consistent fluorescence. In contrast, using labels attached to an antibody without an oligonucleotide as an intermediary link, the distance and orientation of the fluorescent labels to the surface is random, resulting in variable and inconsistent fluorescence (due to interference of the surface with the fluorescence emission).

Other important beneficial differences are that:
1. Oligonucleotides can be used to label a variety of classes of molecules, such as antibodies, nucleic acids, lectins, cell-surface receptors, etc. A single array of first (unlabeled) oligonucleotides, complementary to the labeled oligonucleotide-complexes, can be used as a universal substrate to generate a self-assembling array of these different classes of molecules.
2. The fluorescence characteristics of labels may be affected by the secondary and tertiary conformations and structures of different proteins. This risk is minimized or eliminated by labeling through oligonucleotides.
3. A fluorescent label can be attached to either the immobilized capture oligonucleotide or to its complementary oligonucleotide-antibody complex.

The invention's use of directly attached labels on oligonucleotides does not interfere with the performance, sensitivity, or dynamic range of detection of the target ligand in an assay, while providing a convenient method to monitor the quality of an array from manufacture throughout the actual assay procedure. The CCD camera picture from FIG. 4 shows the invention does not interfere with the performance, sensitivity, or dynamic range of an assay.

Figure 4:
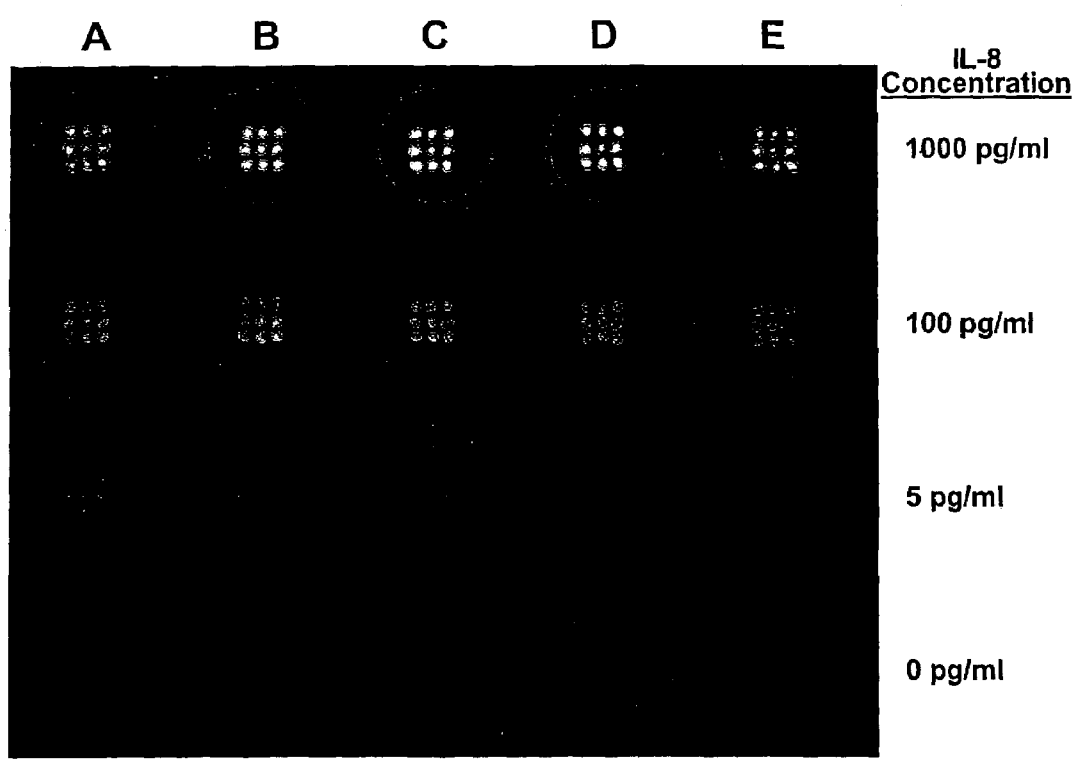
FIG. 4 shows label detection in a sandwich assay using IL-8 antigen as the target ligand with the invention where a CCD camera picture detects and illuminates different concentrations of fluorescent label PBXL-1 corresponding to detector ligand bound in complexes on the surface of a microtiter in a printed 3×3 array pattern.

The CCD camera picture of FIG. 4 shows that the concentration of labeled oligonucleotides did not have an appreciable effect on detection of the IL-8 analyte regardless of the concentration of IL-8 analyte. The detection of IL-8 analyte was consistent. In FIG. 4, columns A–E on the top of the figure correspond to the respective concentrations of Cy3 labeled oligonucleotides from 6 μM, 4 μM, 2 μM, 1 μM, to 0 μM. In FIG. 4, the concentration of IL-8 analyte, the target ligand, ranged from 0 pg/ml to 1000 pg/ml as identified on the right side of the figure. The intensity of the fluorescent emissions or brightness of the spots correlated to detection of the IL-8 analyte.

The protocol for the IL 8 assay shown in FIG. 4 is described below:

Step I. 140 ng/well of antibody-oligonucleotide conjugate in casein buffer were added, and the plate was shook at 37° C. for 1 hour. The plate was washed with wash buffer (0.02% Tween 20 in 1× Tris Buffer Saline) 3 times.

Step II. IL-8 antigen from 1000–0 pg/ml per well in casein buffer was added and reacted at 37° C. for 1 hour and washed with wash buffer 3 times. The concentrations of antigen used in the assay were: 0 pg/ml, 5 pg/ml, 100 pg/ml, and 1000 pg/ml.

Step III. Biotinylated antibody (purchased from R & D Systems, 614 McKinley Place N.E. Minneapolis, Minn. 55413) 50 ng per well was added, incubated at 37° C. for 1 hour, and washed 3 times.

Step IV. Streptavidin PBXL-1 (purchased from Martek, 6480 Dobbin Road. Columbia, Md. 21045) was added (1 mg dissolved in 1 ml of water) 1:150 dilution, 50 Φl/well and incubated at 37° C. for 1 hour and washed 3 times with wash buffer. 50 Φl of wash buffer was kept in each well and imaged using a CCD camera. The CCD camera collected the fluorescent emission at 575 nm that correlated to loading or immobilizing of capture oligonucleotides onto the plate, and the fluorescent emission at 675 nm correlated to the amount of detector antibody bound to the plate.

In the invention, capture oligonucleotides are bound or immobilized onto a solid support. Solid supports capable of having capture oligonucleotides immobilized onto the surface include, but are not limited to polypropylene, polystyrene, glass, nitrocellulose, polyvinylidene fluoride ("PVDF"), and nylon. The solid supports used in the invention may take different forms such as bead, plate, film, or other structures.

Complementary oligonucleotides for the capture oligonucleotides can be directly attached to a variety of different molecules including antigens, antibodies, binding proteins, haptens, hormone receptors, hormones, lectins, carbohydrates, metabolites, drugs, enzyme substrates, and viral proteins for use in the present invention. Complementary oligonucleotides have been directly attached to antibodies to human IL-1b, IL-2, IL-4, IL-6, IL-8, IL-10, IL-12, VEGF, FGF-basic, IFNg, GMCSF, TNF, and used in assays for the invention. The methods for attachment of complementary oligonucleotides to the above antibodies are well known to one of ordinary skill in the art. See e.g., U.S. Pat. No. 5,648,213 (Reddy).

In one aspect of the invention, conditions must be suitable to permit the complementary oligonucleotides to hybridize to capture oligonucleotides to form nucleic acid duplexes. The conditions conducive to the formation of nucleic acid duplexes are well known to one of ordinary skill in the arts (as described, for example, in Sambrook and Russell, *Molecular Cloning: A Laboratory Manual*, 3$^{rd}$ *Edition*, Cold Spring Harbor Laboratory Press, New York, or *Current Protocols in Molecular Biology*, edited by Frederick Ausubel, John Wiley and Sons Publishing, New York, 1987).

Capture and complementary oligonucleotides used in the present invention range from about 15 to about 45 base oligonucleotides. The capture and complementary oligonucleotides preferably each have about 20 to about 30 base oligonucleotides. In one aspect of the present invention a pair of capture and complementary oligonucleotides can be used to capture a single specific target ligand. For example, a pair of capture and complementary oligonucleotides can be used in a well a microtiter plate to capture a specific target ligand in that well.

In another aspect of the invention, an array of different capture and complementary oligonucleotide can be used to capture different target ligands. When using more than one pair of capture and complementary oligonucleotides, the preferred sequences are selected from a group of pairs that do not have substantial cross hybridization. Preferred pairs include:

TABLE 1

| | |
|---|---|
| SEQ ID NO 1: | 5' - GCTTACCGAA TACGGCTTGG AGAACCTATC - 3' |
| SEQ ID NO 2: | 5' - GATAGGTTCT CCAAGCCGTA TTCGGTAAGC - 3' |
| SEQ ID NO 3: | 5' - GCGTGGTCCG CGATCTTCCT ACGATTGATG - 3' |
| SEQ ID NO 4: | 5' - CATCAATCGT AGGAAGATCG CGGACCACGC - 3' |
| SEQ ID NO 5: | 5' - TTTGAGGTTT CGGAGCGTTC CGTGCATCGC - 3' |
| SEQ ID NO 6: | 5' - GCGATGCACG GAACGCTCCG AAACCTCAAA - 3' |
| SEQ ID NO 7: | 5' - CTCATGAAGG CCGTCGGGAA ATTCCAAGTT - 3' |
| SEQ ID NO 8: | 5' - AACTTGGAAT TTCCCGACGG CCTTCATGAG - 3' |
| SEQ ID NO 9: | 5' - TGGATTCCGT TATCACCATT TGGACCCTGC - 3' |
| SEQ ID NO 10: | 5' - GCAGGGTCCA AATGGTGATA ACGGAATCCA - 3' |
| SEQ ID NO 11: | 5' - TACGCTCCCA GTGTGATCAC CAAAGCTTAC - 3' |
| SEQ ID NO 12: | 5' - GTAAGCTTTG GTGATCACAC TGGGAGCGTA - 3' |
| SEQ ID NO 13: | 5' - AGACTGAACT ACCGGCGGTT GCACTACTAA - 3' |
| SEQ ID NO 14: | 5' - GCCAAACACG CCCAATCACT GTTACATGTC - 3' |
| SEQ ID NO 15: | 5' - TTAGTAGTGC AACCGCCGGT AGTTCAGTCT - 3' |
| SEQ ID NO 16: | 5' - GACATGTAAC AGTGATTGGG CGTGTTTGGC - 3' |
| SEQ ID NO 17: | 5' - GCTTGACGTC TACCACCGTG AACATAAGGA - 3' |
| SEQ ID NO 18: | 5' - TCCTTATGTT CACGGTGGTA GACGTCAAGC - 3' |
| SEQ ID NO 19: | 5' - TCGCCAACGT AGCTGTGCTA CAGTTGATTC - 3' |
| SEQ ID NO 20: | 5' - GAATCAACTG TAGCACAGCT ACGTTGGCGA - 3' |
| SEQ ID NO 21: | 5' - GCAGCGGCTA AACCTTGAGA TCGAATGGAA - 3' |
| SEQ ID NO 22: | 5' - TTCCATTCGA TCTCAAGGTT TAGCCGCTGC - 3' |
| SEQ ID NO 23: | 5' - TGCGATATAC TCCATGCCTC TCTTGGCGGA - 3' |
| SEQ ID NO 24: | 5' - TCCGCCAAGA GAGGCATGGA GTATATCGCA - 3' |

For example, an array selected from the above different sequences can be used in a well of a microtiter plate when more than one target ligand is captured in the well.

A variety of different types of detectable labels can be directly attached to the capture or complementary oligonucleotides and used in the present invention. Those detectable labels include but are not limited to fluorophores, radioactive, chemiluminescent, bioluminescent, enzyme, nephelometric, turbidometric, and visible labels. Examples of fluorophores that can be used in the invention include but are not limited to rhodamine 110, rhodal, fluorescein, coumarin, and derivatives of rhodamine 110, rhodal, or fluorescein. Cyanine dyes such as Cy2, Cy3, Cy5, Cy5.5, and Cy7. Examples of radioactive labels that can be used in the invention include but are not limited to $^{32}$P, $^{33}$P, $^{35}$S, $^{3}$H, and $^{125}$I. Examples of chemiluminescent labels that can be used in the invention include but are not limited to acridinium esters, ruthenium complexes, metal complexes, oxalate ester—peroxide combination. Examples of enzyme labels that can be used in the invention include but are not limited to alkaline phosphatase, horseradish peroxidase, beta-galactosidase. Examples of visible labels that can be used in the invention include but are not limited to thiopeptolides, anthroquinone dyes, nitro blue tetrazolium, ortho-nitrophenol β-D-galacto-piranoside (ONPG). The same type of labels, discussed above, can also be used on detector ligands.

Methods for attachment of detectable labels to oligonucleotides are well known to one of ordinary skill in the arts. For example, such methods are described in Yang and Millar, *Methods in Enzymology*, Vol. 278, pages 417–444, 1997.

The system of the present invention can be used in the creation of assay devices, in quality control in the manufacturing process, in quality control in the customer's laboratory, and as a final quality control during the detection of the target ligand in the assay.

An assay device according to the present invention comprises a solid support and a plurality of capture oligonucleotides, wherein at least a portion of the capture oligonucleotides have detectable labels directly attached thereto immobilized onto the solid support. Embodiments of the assay device can include an assay device where: all of the capture oligonucleotides are the same; or all of the detectable labels are the same; or wherein the detectable label is selected from the group consisting of fluorophores, radioactive, chemiluminescent, bioluminescent, enzyme, nephelometric, turbidometric, and visible labels.

An assay kit according to the present invention comprises a solid support; a plurality of capture oligonucleotides immobilized onto the solid support; and a plurality of capture ligands attached to complementary oligonucleotides, wherein at least a portion of the complementary oligonucleotides have detectable labels directly attached thereto. The complementary oligonucleotides in this assay device being capable of hybridizing under appropriate conditions to form double stranded nucleic acid duplexes with the capture oligonucleotides. Embodiments of this assay kit can include an assay device where: all of the capture oligonucleotides are the same; or where the capture ligands are antibodies; or wherein all of the detectable labels are the same; or wherein the capture oligonucleotides and complementary oligonucleotides are in the form of double stranded nucleic acid duplexes.

A sandwich assay method for a target ligand according to the present invention includes the step of providing a solid support having a plurality of capture oligonucleotides immobilized on the solid support. Another step is adding to the solid support of a plurality of capture ligands attached to complementary oligonucleotides, wherein at least a portion of the complementary oligonucleotides have detectable labels directly attached thereto. Another step is providing conditions suitable for hybridization of the complementary oligonucleotides and the capture oligonucleotides to form double stranded nucleic acid duplexes. Another step is to bring the target ligand in contact with the solid support. Another step is adding a plurality of detector ligands having second detectable labels to the solid support. Another step is detecting the first detectable labels, thereby determining the amount of immobilized capture oligonucleotide. Another step is detecting the second detectable labels, thereby determining the amount of the target ligand.

Another sandwich assay method for a target ligand according to the present invention includes the step of providing a solid support having a plurality of capture oligonucleotides immobilized on the solid support, wherein at least a portion of the capture oligonucleotides have detectable labels directly attached thereto. Another step is adding to the solid support a plurality of capture ligands attached to complementary oligonucleotides. Another step is providing conditions suitable for hybridization of the complementary oligonucleotides and the capture oligonucleotides to form double stranded nucleic acid duplexes. Another step is bringing the target ligand in contact with the solid support. Another step is adding a plurality of detector ligands having second detectable labels to the solid support. Another step is detecting the first detectable labels, thereby determining the amount of immobilized capture oligonucleotide. Another step is detecting the second detectable labels, thereby determining the amount of the target ligand.

Embodiments of the sandwich assay described can include: wherein the capture ligands and the detector ligands are antibodies; or wherein the capture ligands and the detector ligands are antigens; or wherein the step of detecting the first and second detectable labels is by quantitatively measuring each label; or wherein the step of adding a plurality of detector ligands occurs before the step of providing conditions suitable for hybridization; or wherein the detectable label is selected from the group consisting of fluorophores, radioactive, chemiluminescent, bioluminescent, enzyme, nephelometric, turbidometric, and visible labels.

A competitive assay method for a target ligand according to the present invention includes the step of providing a solid support having a plurality of capture oligonucleotides immobilized on the solid support. Another step is adding to the solid support a plurality of capture ligands attached to complementary oligonucleotides, wherein at least a portion of the complementary oligonucleotides have first detectable labels directly attached thereto. Another step is providing conditions suitable for hybridization of the complementary oligonucleotides and the capture oligonucleotides to form double stranded nucleic acid duplexes. Another step is adding the target ligand to the solid support, wherein the target ligand competes with the detector ligand in binding to the capture ligand. Another step is adding a plurality of detector ligands having second detectable labels to the solid support. Another step is detecting the first detectable labels, thereby determining the amount of immobilized capture oligonucleotide. Another step is detecting the second detectable labels, thereby determining the amount of the target ligand.

Another competitive assay method for a target ligand according to the present invention includes the step of providing a solid support having a plurality of capture oligonucleotides immobilized on the solid support, wherein at least a portion of the capture oligonucleotides have first detectable labels directly attached thereto. Another step is adding to the solid support, a plurality of capture ligands attached to complementary oligonucleotides. Another step is providing conditions suitable for hybridization of the complementary oligonucleotides and the capture oligonucleotides to form double stranded nucleic acid duplexes. Another step is adding the target ligand onto the solid support, wherein the target ligand competes with the detector ligand in binding to the capture ligand. Another step is adding a plurality of detector ligands having second detectable labels onto the solid support. Another step is detecting the first detectable labels, thereby determining the amount of immobilized capture oligonucleotide. Another step is detecting the second detectable labels, thereby determining the amount of the target ligand In a preferred embodiment of any of the assay methods described above (i.e. sandwich assay or competitive assay), the first and second detectable labels are fluorophores that use the same excitation light source wavelength. The fluorophores typically have different emission wavelengths. The operator of the assay can use the same excitation light source, and determine the quality of the assay's capture components, labeled oligonucleotides immobilized on the solid support, and the concentration of the target ligand, by independently measuring the emission wavelength of each fluorophore.

In a preferred embodiment of any of the assay methods described above (i.e. sandwich assay or competitive assay), the steps of detecting the first detectable labels and detecting the second detectable labels are simultaneous.

Figure 2:
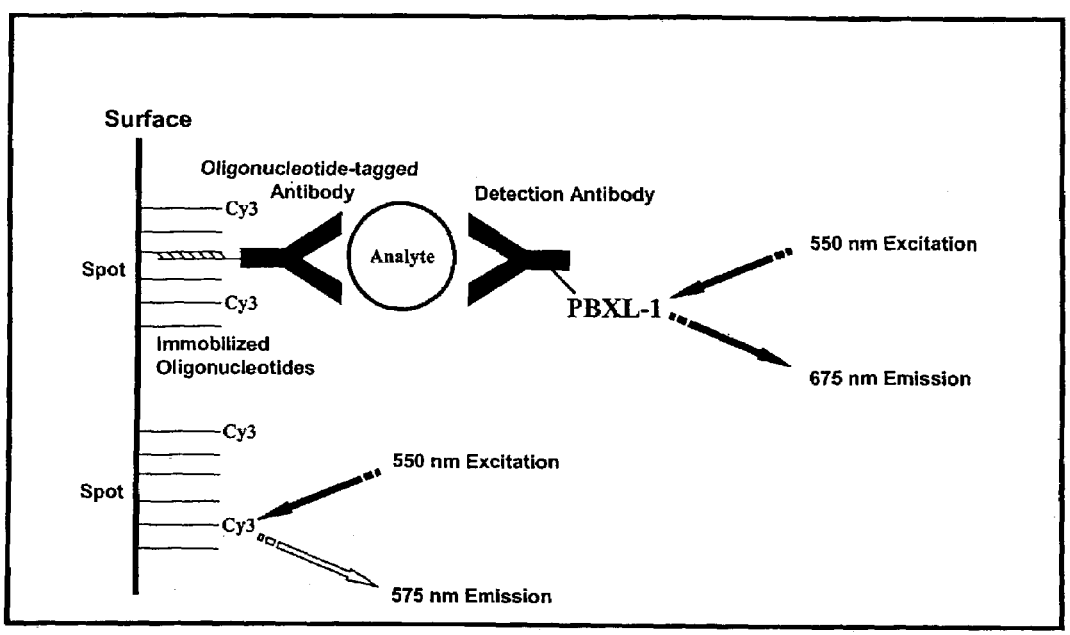
FIG. 2 depicts a sandwich assay of the invention using a plurality of immobilized capture oligonucleotides, wherein at least a portion having directly attached fluorescent label Cy3; an oligonucleotide-tagged antibody, wherein the oligonucleotide is complementary to the capture oligonucleotide; an analyte, and a PBXL-1 tagged detection antibody.
Figure 3:
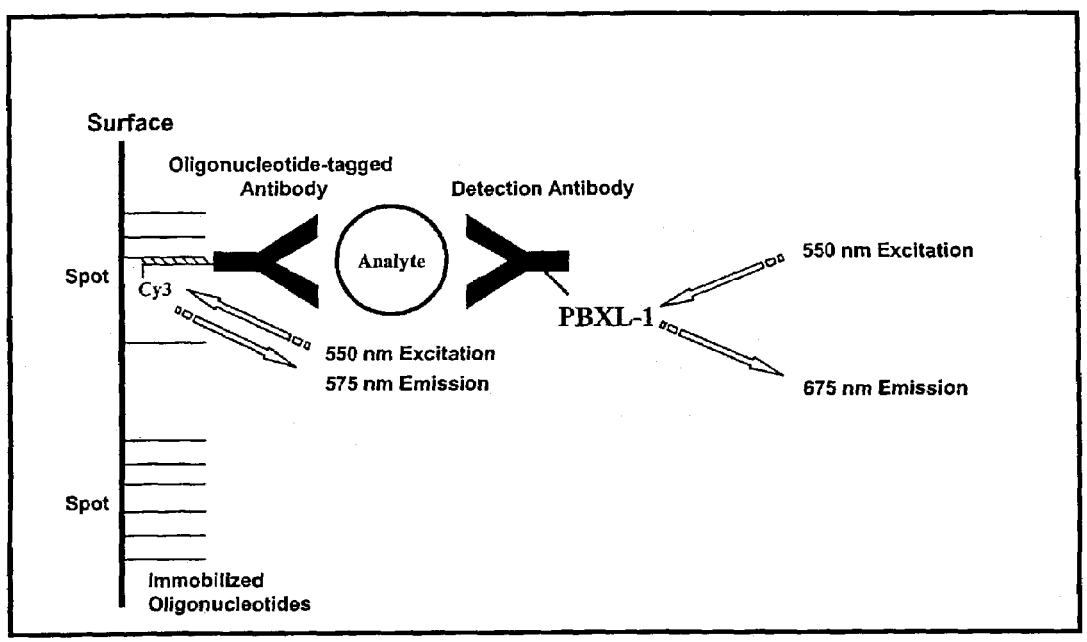
FIG. 3 depicts a sandwich assay of the invention using immobilized capture oligonucleotides; a Cy3 labeled oligonucleotide-tagged antibody, wherein the oligonucleotide is complementary to the capture oligonucleotide; an analyte; and a PBXL-1 tagged detection antibody.

Preferred embodiments of sandwich assays of the invention are depicted in FIGS. 2 and 3. In both embodiments, Cy3 labeled oligonucleotides and PBXL-1 labeled detection antibody are the first and second detectable labels, and these respective labels use the same excitation wavelength of 550 nm. However, the Cy3 label directly attached to the oligonucleotides has an emission wavelength of 575 nm, whereas the PBXL-1 label has an emission wavelength of 675 nm. Therefore, when an excitation wavelength of 550 nm is used, detection and measurement of both labels can result because each label has a different emission wavelength.

The difference between the embodiments shown in FIGS. 2 and 3 is which oligonucleotide has the directly attached Cy3 label. In FIG. 2, the Cy3 label is directly attached to the capture oligonucleotide immobilized on the surface, whereas the complementary oligonucleotide attached to the antibody (capture ligand) does not have the Cy3 label. In FIG. 3, the reverse situation occurs wherein the Cy3 label is directly attached to the complementary oligonucleotide attached to an antibody, and the capture oligonucleotide immobilized on the surface is unlabeled. In FIGS. 2 and 3, the same detector ligand, a detection antibody labeled with PBXL-1, is depicted.

FIG. 7 depicts a preferred embodiment of a competitive assay of the present invention using immobilized capture oligonucleotides; a Cy3 labeled oligonucleotide-tagged antibody, wherein the oligonucleotide is complementary to the capture oligonucleotide; a target analyte; and a competing PBXL-1 labeled analyte. In FIG. 7, the detector ligand is called the "competing labeled analyte", and the "target ligand" is called the target analyte.

As one of ordinary skill in the art will know, there are several types of fluorescent or other labels that can be used in this manner. For example, the following pairs of labels can be used: fluorescein and rhodamine; Cy3 and Cy5; PBXL-1 and Cy5.5; and fluorescein and PBXL-1.

The assay devices, method of manufacturing, and assays for target ligands can use the same capture oligonucleotides and complementary oligonucleotides or combinations of different capture oligonucleotides and their respective complementary oligonucleotides. One of ordinary skill in the art will know how to prepare a variety of assays, including but not limited to sandwich and competitive assays, according to the present invention.

A variety of different permutations of the invention is contemplated, and not meant to be limited by this disclosure. The present invention is not limited to the preferred embodiments described in this section. The embodiments are merely exemplary, and one skilled in the art will recognize that many others are possible in accordance with this invention. Having now generally described the invention, the same will be more readily understood through references to the following examples, which are provide by way of illustration, and are not intended to be limiting of the present invention, unless so specified.

EXAMPLE 1

Immobilizing Capture Oligonucleotides with Directly Attached Cy3 Label onto a Microtiter Plate, and Detecting the Directly Attached Cy3 Label A. Synthesis of 5'-Dye-Label 3'-Amino Capture Oligonucleotides with Directly Attached Cy3 Labels A 30-mer oligonucleotide was synthesized on a 3'-amino-modifier C7 CPG (Glen Research Part # 20-2957-01, purchased from Glen Research, Sterling, Va.) on 1 μmole scale (coupling efficiency≅98%) on ABI 394 (purchased from Applied Biosystems, 850 Lincoln Center Drive, Foster City, Calif. 94404) using $A^{pac}$, $G^{ipr-pac}$, $C^{ac}$ and T phosphoramdites. At the 5' end, dye phosphoramidite Cy3 (purchased from Glen research, Sterling, Va.) was coupled using the standard protocol recommended by the supplier of the reagents.

Next, the oligonucleotide was cleaved and deprotected using ammonia for 24 hours at room temperature and purified on polypak cartridges (Glen Research, Sterling, Va.). The dye labeled oligonucleotide was analyzed on CE (Beckman Pace 5000, with SSDNA gel kit).

B. Immobilization & Detection of Capture Oligonucleotides Attached to Microtiter Plates The activation and chemical derivitization of polypropylene microtiter plates is described in patent application Ser. No. 10/033,308 filed Oct. 24, 2001, incorporated in its entirety by reference herein. The application describes the immobilization of amino oligonucleotides used in this example.

In brief, the wells of polypropylene microtiter plates were aminated by radio frequency plasma discharge treatment under an ammonia atmosphere using a Plasma Science Model PS0150 RFPD generator system. The aminated plates were then succinylated by treatment with 0.1 M succinic anhydride in 0.1 M sodium acetate for 20 hrs, followed by 3 washes with 0.1 M sodium acetate and 3 washes with isopropyl alcohol. Succinylated plates were then reacted for 2 hrs with 250 mM triazole in acetonitrile containing 3% triethylamine, followed by 3 washes with acetonitrile. Capture oligonucleotides were chemically coupled to the surface of the activated plates by depositing approximately 10 nl spots of 20 μM solution of the capture oligonucleotides containing about 0 to about 6 μM of Cy3-labeled oligonucleotides, onto the bottom surface of a microtiter plate in a 3×3 microarray pattern. A Biomek 2000 high-density replicating tool (Beckman Coulter, Fullerton, Calif.) or a ProSys Gantry System (Cartesian Technologies, Irvine, Calif.) were used to deposit the spots in microarrays.

The plates were incubated 16 hr at room temperature in a humidified chamber. The plates were then 'quenched' by incubating in a 1% casein solution in carbonate buffer, pH 9.3, for 1 hour to bind to any amino-reactive groups remaining on the plate surface. The plates were then washed with water, followed by a wash with TE buffer (10 mM Tris, pH 7.5, 1 mM EDTA).

Figure 1:
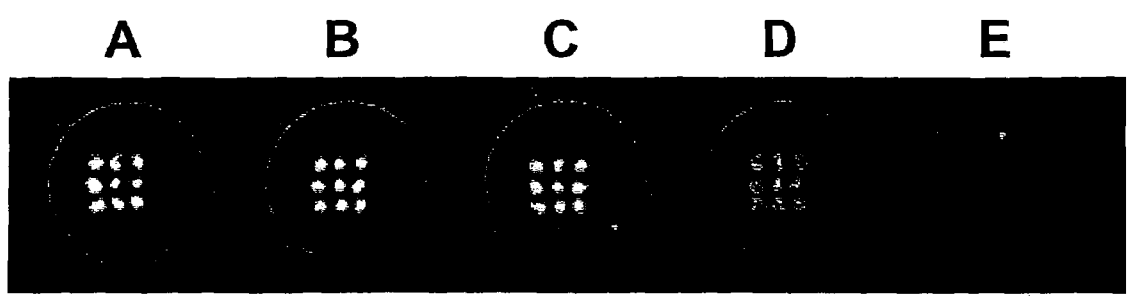
FIG. 1 shows label detection using the invention where a CCD camera picture detects and illuminates different concentrations of fluorescent label Cy3 directly attached to 30-base capture oligonucleotides immobilized onto the bottom surface of a microtiter in a printed 3×3 array pattern.

The microarrays were illuminated with a 550 nm light source and visualized with a charge coupled device camera ("CCD camera"). The CCD camera used was a Photometrics CoolSNAP camera (Roper Scientific, Tucson, Ariz.) mounted with a 575 nm emission filter. FIG. 1 shows the CCD camera picture illustrating the emissions from labels of the capture oligonucleotides having concentrations of 6 µM, 4 µM, 2 µM, 1 µM, and 0 µM of Cy3-labeled oligonucleotides identified by Columns A, B, C, D, and E respectively.

EXAMPLE 2

Immobilizing Capture Oligonucleotides with Directly Attached Cy3.5, or Cy5, or Cy5.5 Labels onto a Microtiter Plate, and Detecting the Directly Attached Cy3.5, or Cy5, or Cy5.5 Labels In other experiments, the same procedure described in Example 1 was used except that Cy3.5 or Cy5 or Cy5.5 labels were used in place of Cy3 labels. At the 5' end, Cy3.5 or Cy5 or Cy5.5 labels (purchased from Glen research, Sterling, Va.) were coupled using the standard protocol recommended by the supplier of the reagents. The Cy3.5, or Cy5, or Cy5.5 labels were subsequently detected using the CCD camera similar to the manner described in Example 1. The difference being that each label's specific excitation wavelength and emission wavelength for replaced the Cy3 wavelengths identified in Example 1.

EXAMPLE 3

Immobilizing Capture Oligonucleotides onto a Microtiter Plate, Hybridizing Complementary Oligonucleotides with Directly Attached Labels, and Detecting the Directly Attached Labels in the Duplexes A. Synthesis of Unlabeled 5'-3'-amino Capture Oligonucleotide.

Example 1 (above) described the basic procedure for synthesis of amino-oligonucleotide. That procedure was used in this example except that unlabeled nucleotides were used for the terminal base in place of a label B. Imobilization of Capture Amino Oligonucleotide onto a Microtiter Plate The immobilization of capture oligonucleotides onto a microtiter plate as used in this example is the procedure described under Example 1. The plates were then 'quenched' by incubating in a 1% casein solution in carbonate buffer, pH 9.3, for 1 hour to bind to any amino-reactive groups remaining on the plate surface. The plates were then washed with water, followed by a wash with TE buffer (10 mM Tris, pH 7.5, 1 mM EDTA).

C. Synthesis of Labeled Complementary Oligonucleotide

Example 1 (above) described the basic procedure for synthesis of Cy3 dye labeled amino-oligonucleotides that was also used in this example.

D. Mixing the Immobilized Capture Oligonucleotides with Complementary Oligonucleotides under Suitable Conditions to form Nucleic Acid Duplexes 50 µl of 10 nM complementary oligonucleotides in casein buffer was added to the immobilized capture oligonucleotides. This step was performed under conditions typical for a normal immunoassay binding step (i.e. moderate salt and temperature conditions), partly to protect the structure and integrity of the antibody portion of the complex, and partly for ease of use.

E. Detection of Complementary Oligonucleotides to Determine Immobilized Capture Oligonucleotides The microarrays were illuminated with a 550 nm light source and visualized with a CCD camera. The CCD camera used was a Photometrics CoolSNAP camera (Roper Scientific, Tucson, Ariz.) mounted with a 575 nm emission filter.

EXAMPLE 4

A Sandwich Assay Using Cy3 Labeled Capture Oligonucleotides, IL-8 Antibodies Conjugated to Complementary Oligonucleotides, Detector Ligands with PBXL-1 Labels, and IL-8 Antigens The procedure described in Example 1 was used to synthesize and immobilize arrays of capture oligonucleotide with directly attached Cy3 labels onto a microtiter plate. The complementary oligonucleotides were synthesized by the same procedure as the labeled oligonucleotides except that unlabeled nucleotides were used for the terminal base, and attached to the capture antibody.

The protocol for the attachment of oligonucleotide to antibody, discussed in U.S. Pat. No. 5,648,213, which is incorporated by reference herein, was used for this example. For the IL-8 assay, the target ligand was IL-8 antigen, the capture ligand was an IL-8 antibody conjugated to an oligonucleotide that is complementary to capture oligonucleotides of an immobilized array, and the detector ligands were IL-8 antibodies labeled with PBXL-1 (a fluorescent dye purchased from Martek Biosciences Corp.; Columbia, Md.). The detector ligands, IL-8 antibodies, were labeled with PBXL-1 through a biotin-streptavidin interaction by mixing: IL-8 detection antibodies that were covalently coupled to biotin (as supplied by the manufacturer, R & D Systems); and PBXL-1 that was supplied as a streptavidin conjugate supplied by the manufacturer, Martek.

50 µl of 10 nM of IL-8 antibody conjugated to an oligonucleotide that is complementary to capture oligonucleotides in casein buffer was added to the immobilized capture oligonucleotides. This step was performed under conditions typical for a normal immunoassay binding step (i.e. moderate salt and temperature conditions), partly to protect the structure and integrity of the antibody portion of the conjugate, and partly for ease of use.

Concentrations of IL-8 antigen ranging from 1000–0 pg/ml per well in casein buffer were added and reacted at 37° C. for 1 hour and washed with wash buffer 3 times. The concentrations of IL-8 antigen used in the assay were: 0 pg/ml, 5 pg/ml, 100 pg/ml, and 1000 pg/ml.

Wells were incubated with 50 ng biotinylated IL-8 antibody for 1 hr at 37° C., washed 3 times with wash buffer, then incubated with streptavidin-PBXL-1 for 1 hr at 37° C., and washed 3 times with wash buffer.

The plates were illuminated with a single excitation light source of 550 nm. The plates were visualized with a CCD camera mounted with a 675 nm emission filter to detect bound IL-8 detector antibodies. The plates were also visualized with a CCD camera mounted with a 575 nm emission filter to detect the immobilized capture oligonucleotides.

FIG. 4 shows the CCD camera picture illustrating the emissions from PBXL-1 labels of the bound IL-8 detector antibodies for each concentrations of IL-8 antigen. On the right side of the picture is the IL-8 antigen concentration, and top columns A, B, C, D, and E of the picture respectively correspond to 6 µM, 4 µM, 2 µM, 1 µM, and 0 µM of Cy3 labeled capture oligonucleotides. Whereas, FIG. 1 shows the CCD camera picture illustrating the emissions from Cy3 labeled capture oligonucleotides from the same plate used in this example.

EXAMPLE 5

A Sandwich Assay Using Cy5.5 Labeled Capture Oligonucleotides, IL-8 Antibodies Conjugated to Complementary Oligonucleotides, Detector Ligands with PBXL-1 Labels, and IL-8 Antigens The procedure described in Example 1 was used to synthesize and immobilize arrays of capture oligonucleotide with directly attached Cy5.5 label, instead of the Cy3 label used in Example 1, onto a microtiter plate. The complementary oligonucleotides were synthesized by the same method as the labeled oligonucleotides except that unlabeled nucleotides were used for the terminal base, and attached to the capture antibody.

The protocol for attachment of complementary oligonucleotide to IL-8 antibody for the IL-8 assay was discussed in U.S. Pat. No. 5,648,213, which is incorporated by reference herein, and was used for this example. The target ligand was IL-8 antigen, the capture ligand was an IL-8 antibody conjugated to an oligonucleotide that is complementary to capture oligonucleotides of an immobilized array, and the detector ligands were IL-8 antibodies labeled with PBXL-1 (a fluorescent dye purchased from Martek Biosciences Corp.; Columbia, Md.). The detector ligands, IL-8 antibodies, were labeled with PBXL-1—1 through a biotin-streptavidin interaction by mixing: IL-8 detector antibodies that were covalently coupled to biotin (as supplied by the manufacturer, R & D Systems); and PBXL-1 that was supplied as a streptavidin conjugate supplied by the manufacturer, Martek.

50 µl of 10 nM of IL-8 antibody conjugated to an oligonucleotide that is complementary to capture oligonucleotides in casein buffer was added to the immobilized capture oligonucleotides. This step was performed under conditions typical for a normal immunoassay binding step (i.e. moderate salt and temperature conditions), partly to protect the structure and integrity of the antibody portion of the conjugate, and partly for ease of use.

Concentrations of IL-8 antigen ranging from 250–0 pg/ml per well in casein buffer were added and reacted at 37° C. for 1 hour and washed with wash buffer 3 times. The concentrations of IL-8 antigen used in the assay were: 0 pg/ml, 1 pg/ml, 2 pg/ml, 5 pg/ml, 10 pg/ml, 25 pg/ml, 100 pg/ml, and 250 pg/ml.

Wells were incubated with 50 ng biotinylated IL-8 antibody for 1 hr at 37° C., washed 3 times with wash buffer, then incubated with streptavidin-PBXL-1 for 1 hr at 37° C., and washed 3 times with wash buffer.

The plates were illuminated using a light source with 680 nm excitation filter and visualized with a CCD camera mounted with a 715 nm emission filter to detect Cy5.5 emission of immobilized capture oligonucleotides. The plates were illuminated using a light source with 550 nm excitation filter and visualized with a CCD camera mounted with a 675 nm emission filter to detect PBXL-1 emission of bound IL-8 detector antibodies.

FIG. 5 shows the CCD camera picture illustrating the emissions from the Cy5.5 labels of the capture oligonucleotides on the left side, and emissions from PBXL-1 labels of the bound IL-8 detector antibodies on the right side.

EXAMPLE 6

A Sandwich Assay Using Capture Oligonucleotides; Cy5.5 Labeled Complementary Oligonucleotides Conjugated to Antibodies; Detector Ligands with PBXL-1, and IL-2, IL-8, IL-12, Interferon-Gamma, FGF-Basic, and GMCSF Antigens as Target Ligands A. Synthesis of Unlabeled 5'-3'-amino Capture Oligonucleotides Example 1 (above) described the basic procedure for synthesis of amino-oligonucleotide. That procedure was used in this example except that unlabeled nucleotides were used for the terminal base in place of a label.

B. Synthesis of Labeled Complementary Oligonucleotide

Example 3 (above) described the basic procedure for synthesis of dye labeled amino-oligonucleotides that was also used in this example. In this example, Cy5.5 was the directly attached label, for complementary oligonucleotides, used instead of Cy3 label.

C. Seven Different Capture/Complementary Oligonucleotide Pairs were Prepared and Used from a List of Preferred Oligonucleotide Pairs A different capture and complementary oligonucleotide sequence was used for each of the target ligands tested in this example: IL-2, IL-8, IL-12, Interferon-gamma, FGF-basic, GMCSF antigens, and an internal control antigen, used in this example. Seven different preferred pairs of capture and complementary oligonucleotides were used in this example. The seven pairs were selected from a list of preferred sequence pairs because the sequences do not substantially cross hybridize when used together in an assay. The list of preferred pair was previously identified.

D. Immobilization of Capture Amino Oligonucleotide in a Microarray onto a Microtiter Plate The immobilization of capture oligonucleotides onto a microtiter plate as used in this example was the basic procedure described under Example 1 and 3. In this example, each of the six different capture oligonucleotides were immobilized at predetermined spots in the microarray to correspond to the specific antigen or target ligand.

A different antigen (not one of the six target antigens), chicken ovalbumin, was used as an internal control, and the seventh different capture oligonucleotide was immobilized in three corner positions. This internal control is shown in the picture in FIG. 6 as the brightest PBXL-1 emissions at three corner positions in the 0 pg/ml and 2 pg/ml concentrations of the target antigens.

E. Preparation of Capture Ligands and Detector Ligands

The capture ligand used in this example for an IL-8 antigen was an IL-8 antibody. The IL-8 antibody was conjugated to an oligonucleotide that is complementary to its respective capture oligonucleotide in immobilized microarray. The detector ligands for IL-8 antigens were IL-8 antibodies labeled with PBXL-1 (a fluorescent dye purchased from Martek Biosciences Corp.; Columbia, Md.). The detector ligands, IL-8 antibodies, were labeled with PBXL-1—1 through a biotin-streptavidin interaction by mixing: IL-8 detector antibodies that were covalently coupled to biotin (as supplied by the manufacturer, R & D Systems); and PBXL-1 that was supplied as a streptavidin conjugate supplied by the manufacturer, Martek.

The capture ligands and detector ligands for the remaining antigens were made using the same process described for the IL-8. In place of IL-8 antibodies, the respective antibodies for IL-2, IL-12, Interferon-gamma, FGF-basic, and GMCSF were used to create the necessary components of the sandwich.

F. IL-8 Assay Protocol Used

The basic protocol for the IL 8 assay discussed in Example 4 was used for this example. However, in addition to IL-8 antigen, the following target ligands were also used in this example: IL-2, IL-12, Interferon-gamma, FGF-basic, and GMCSF antigens.

The first step in the assay was the immobilization of the capture oligonucleotides in a predetermined microarray as described in the section on immobilizing capture oligonucleotides.

The second step was the addition of about 50 µl of 10 nM capture ligands having complementary oligonucleotides, prepared as described in the preceding section, in casein buffer to the immobilized capture oligonucleotides in the wells of the microtiter plate. This step was performed under conditions typical for a normal immunoassay binding step (i.e. moderate salt and temperature conditions), partly to protect the structure and integrity of the antibody portion of the conjugate, and partly for ease of use.

The third step involved the addition of the specific concentrations of IL-2, IL-8, IL-12, Interferon-gamma, FGF-basic, and GMCSF antigens to the wells. The concentrations of each antigen used in the assay were: 0 pg/ml, 2 pg/ml, 10 pg/ml, 100 pg/ml, 400 pg/ml, and 1000 pg/ml. The added antigen in casein buffer were reacted at 37° C. for 1 hour and washed with wash buffer 3 times.

The fourth step was the addition of the detector ligands for each antigen, prepared as described in the preceding section, to the wells of the microtiter plate.

Wells were incubated with biotinylated antibodies for each antigen, then PBXL-1 as described in examples above.

The plates were illuminated using a light source with 680 nm excitation filter and visualized with a CCD camera mounted with a 715 nm emission filter to detect Cy5.5 emission of immobilized capture oligonucleotides. The plates were illuminated using a light source with 550 nm excitation filter and visualized with a CCD camera mounted with a 675 nm emission filter to detect PBXL-1 emission of bound IL-2, IL-8, IL-12, Interferon-gamma, FGF-basic, and GMCSF antigens.

FIG. 6 shows the CCD camera picture illustrating the Cy5.5 emissions from the complementary oligonucleotides on the left side, and PBXL-1 emissions from the bound detector antibodies for IL-2, IL-8, IL-12, Interferon-gamma, FGF-basic, and GMCSF antigens on the right side. The analyte (or antigen) concentration is identified to the right of the picture illustrating the PBXL-1 emissions.

Having thus described the invention, it should be apparent that numerous modifications and adaptations may be resorted to without departing from the scope and fair meaning of the instant invention as set forth hereinabove and as described hereinbelow by the claims.

Although the present invention has been described in considerable detail with reference to certain preferred versions thereof, other versions are possible. Therefore, the spirit and scope of the appended claims should not be limited to the description of the preferred versions described herein.

All features disclosed in the specification, including the claims, abstracts, and drawings, and all the steps in any method or process disclosed, may be combined in any combination, except combinations where at least some of such features and/or steps are mutually exclusive. Each feature disclosed in the specification, including the claims, abstract, and drawings, can be replaced by alternative features serving the same, equivalent or similar purpose, unless expressly stated otherwise. Thus, unless expressly stated otherwise, each feature disclosed is one example only of a generic series of equivalent or similar features.

Any element in a claim that does not explicitly state "means" for performing a specified function or "step" for performing a specified function, should not be interpreted as a "means" or "step" clause as specified in 35 U.S.C. § 112.

What is claimed is:

1. An assay method for a target ligand comprising the steps of:
   a) providing a solid support having a plurality of capture oligonucleotides immobilized on the solid support;
   b) adding to the solid support a plurality of capture ligands attached to complementary oligonucleotides, wherein at least a portion of the complementary oligonucleotides have first detectable labels directly attached thereto and the capture ligands are antibodies or antigens;
   c) providing conditions suitable for hybridization of the capture oligonucleotides and the complementary oligonucleotides to form double stranded nucleic acid duplexes;
   d) bringing the target ligand in contact with the solid support under conditions whereby the target ligand binds to the capture ligand to form a first complex;
   e) adding a plurality of detector ligands having second detectable labels to the solid support under conditions whereby the one or more than one detector ligand binds to the target ligand to form a second complex;
   f) detecting the first detectable labels; and
   g) detecting the second detectable labels in the second complex, thereby detecting the target ligand.

2. The method of claim 1 wherein the plurality of capture oligonucleotides are the same.

3. The method of claim 1 wherein at least some of the plurality of capture oligonucleotides are different.

4. The method of claim 1 wherein the detector ligands are antibodies.

5. The method of claim 1 wherein the detector ligands are antigens.

6. The method of claim 1 wherein the step of adding a plurality of detector ligands occurs before the step of providing conditions suitable for hybridization.

7. The method of claim 1 wherein the steps of detecting the first and second detectable labels are by quantitatively measuring each label.

8. The method of claim 1 wherein the first and second detectable labels are each selected from the group consisting of fluorophores, radioactive, chemiluminescent, bioluminescent, enzyme, nephelometric, turbidometric, and visible labels.

9. The method of claim 1 wherein the first and second detectable labels are fluorophores that use the same excitation light source.

10. The method of claim 9 wherein the steps of detecting the first detectable labels and detecting the second detectable labels are simultaneous.

11. The method of clam 1 wherein the first and second detectable labels are different.

12. The method of claim 1 where the target ligands, capture ligands and detection ligands are different from each other.

13. An assay method for a target ligand comprising the steps of:
   a) providing a solid support having a plurality of capture oligonucleotides immobilized on the solid support, wherein at least a portion of the capture oligonucleotides have first detectable labels directly attached thereto;
   b) adding to the solid support a plurality of capture ligands attached to complementary oligonucleotides wherein the capture ligands are antibodies or antigens;
   c) providing conditions suitable for hybridization of the capture oligonucleotides and the complementary oligonucleotides to form double stranded nucleic acid duplexes;
   d) bringing the target ligand in contact with the solid support under conditions whereby the target ligand binds to the capture ligand to form a first complex;
   e) adding a plurality of detector ligands having second detectable labels to the solid support under conditions whereby the one or more than one detector ligand binds to the target ligand to form a second complex;
   f) detecting a first signal caused by the first detectable labels; and
   g) detecting a second signal caused by the second detectable labels in the second complex, the first and second signals being different from each other, thereby detecting the target ligand.

14. The method of claim 13 wherein the plurality of capture oligonucleotides are the same.

15. The method of claim 13 wherein at least some of the plurality of capture oligonucleotides are different.

16. The method of claim 13 wherein the detector ligands are antibodies.

17. The method of claim 13 wherein the detector ligands are antigens.

18. The method of claim 13 wherein the step of adding a plurality of detector ligands occurs before the step of providing conditions suitable for hybridization.

19. The method of claim 13 wherein the steps of detecting the first and second detectable labels are by quantitatively measuring each label.

20. The method of claim 13 wherein the first and second detectable labels are each selected from the group consisting of fluorophores, radioactive, chemiluminescent, bioluminescent, enzyme, nephelometric, turbidometric, and visible labels.

21. The method of claim 13 wherein the first and second detectable labels are fluorophores that use the same excitation light source.

22. The method of claim 21 wherein the steps of detecting the first detectable labels and detecting the second detectable labels are simultaneous.

23. The method of claim 13 where the target ligands, capture ligands and detection ligands are different from each other.

24. An assay method for a target ligand comprising the steps of:
   a) providing a solid support having a plurality of capture oligonucleotides immobilized on the solid support;
   b) adding to the solid support a plurality of capture ligands attached to complementary oligonucleotides, wherein at least a portion of the complementary oligonucleotides have first detectable labels directly attached thereto;
   c) providing conditions suitable for hybridization of the capture oligonucleotides and complementary oligonucleotides to form double stranded nucleic acid duplexes;
   d) adding a plurality of detector ligands having second detectable labels onto the solid support;
   e) adding an unlabeled target ligand onto the solid support, wherein the unlabeled target ligand competes with the detector ligand in binding to the capture ligand;
   f) detecting the first detectable label; and
   g) detecting and measuring a second signal caused by the second detectable labels of the detector ligands bound to the capture ligand, under conditions whereby the quantity of the second detectable signal detected is inversely proportional to the amount of unlabeled target ligand bound to the capture ligand, thereby determining the quantity of target ligand.

25. The method of claim 24 wherein the plurality of capture oligonucleotides are the same.

26. The method of claim 24 wherein at least some of the plurality of capture oligonucleotides are different.

27. The method of claim 24 wherein the steps of detecting the first and second detectable tables are by quantitatively measuring each label.

28. The method of claim 24 wherein the first and second detectable labels are fluorophores that use the same excitation light source.

29. The method of claim 28 wherein the steps of detecting the first detectable labels and detecting the second detectable labels are simultaneous.

30. The method of clam 24 wherein the first and second detectable labels are different.

31. The method of claim 24 where the target ligands, capture ligands and detection ligands are different from each other.

32. An assay method for a target ligand comprising the steps of:
   a) providing a solid support having a plurality of capture oligonucleotides immobilized on the solid support, wherein at least a portion of the capture oligonucleotides have first detectable labels directly attached thereto;
   b) adding onto the solid support a plurality of captures capture ligands attached to complementary oligonucleotides;
   c) providing conditions suitable for hybridization of the capture oligonucleotides and complementary oligonucleotides to form double stranded nucleic acid duplexes;
   d) adding a plurality of detector ligands having second detectable labels onto the solid support;
   e) adding an unlabeled target ligand onto the solid support, wherein the unlabeled target ligand competes with the detector ligand in binding to the capture ligand;
   f) detecting a first signal caused by the first detectable labels; and
   g) detecting and measuring a second signal caused by the second detectable labels of the detector ligands bound to the capture ligand, wherein the first and second signals are different from each other, under conditions whereby the quantity of the second signal detected is inversely proportional to the amount of unlabeled target ligand bound to the capture ligand, thereby determining the quantity of target ligand.

33. The method of claim 32 wherein the plurality of capture oligonucleotides are the same.

34. The method of claim 32 wherein at least some of the plurality of capture oligonucleotides are different.

35. The method of claim 32 wherein the steps of detecting the first and second detectable labels are by quantitatively measuring each label.

36. The method of claim 32 wherein the first and second detectable labels are fluorophores that use the same excitation light source.

37. The method of claim 36 wherein the steps of detecting the first detectable labels and detecting the second detectable labels are simultaneous.

38. The method of claim 32 where the target ligands, capture ligands and detection ligands are different from each other.

* * * * *

SEQUENCE LISTING

```
<160> NUMBER OF SEQ ID NOS: 24

<210> SEQ ID NO 1
<211> LENGTH: 30
<212> TYPE: DNA
<213> ORGANISM: Artificial
<220> FEATURE:
<223> OTHER INFORMATION: completely synthesized

<400> SEQUENCE: 1
gcttaccgaa tacggcttgg agaacctatc                                    30

<210> SEQ ID NO 2
<211> LENGTH: 30
<212> TYPE: DNA
<213> ORGANISM: Artificial
<220> FEATURE:
<223> OTHER INFORMATION: completely synthesized

<400> SEQUENCE: 2
gataggttct ccaagccgta ttcggtaagc                                    30

<210> SEQ ID NO 3
<211> LENGTH: 30
<212> TYPE: DNA
<213> ORGANISM: Artificial
<220> FEATURE:
<223> OTHER INFORMATION: completely synthesized
```

<400> SEQUENCE: 3
gcgtggtccg cgatcttcct acgattgatg                           30

<210> SEQ ID NO 4
<211> LENGTH: 30
<212> TYPE: DNA
<213> ORGANISM: Artificial
<220> FEATURE:
<223> OTHER INFORMATION: completely synthesized

<400> SEQUENCE: 4
catcaatcgt aggaagatcg cggaccacgc                           30

<210> SEQ ID NO 5
<211> LENGTH: 30
<212> TYPE: DNA
<213> ORGANISM: Artificial
<220> FEATURE:
<223> OTHER INFORMATION: completely synthesized

<400> SEQUENCE: 5
tttgaggttt cggagcgttc cgtgcatcgc                           30

<210> SEQ ID NO 6
<211> LENGTH: 30
<212> TYPE: DNA
<213> ORGANISM: Artificial
<220> FEATURE:
<223> OTHER INFORMATION: completely synthesized

<400> SEQUENCE: 6
gcgatgcacg gaacgctccg aaacctcaaa                           30

<210> SEQ ID NO 7
<211> LENGTH: 30
<212> TYPE: DNA
<213> ORGANISM: Artificial
<220> FEATURE:
<223> OTHER INFORMATION: completely synthesized

<400> SEQUENCE: 7
ctcatgaagg ccgtcgggaa attccaagtt                           30

<210> SEQ ID NO 8
<211> LENGTH: 30
<212> TYPE: DNA
<213> ORGANISM: Artificial
<220> FEATURE:
<223> OTHER INFORMATION: completely synthesized

<400> SEQUENCE: 8
aacttggaat tcccgacgg ccttcatgag                            30

<210> SEQ ID NO 9
<211> LENGTH: 30
<212> TYPE: DNA
<213> ORGANISM: Artificial
<220> FEATURE:
<223> OTHER INFORMATION: completely synthesized

<400> SEQUENCE: 9
tggattccgt tatcaccatt tggaccctgc                           30

<210> SEQ ID NO 10

```
<211> LENGTH: 30
<212> TYPE: DNA
<213> ORGANISM: Artificial
<220> FEATURE:
<223> OTHER INFORMATION: completely synthesized

<400> SEQUENCE: 10
gcagggtcca aatggtgata acggaatcca                                      30

<210> SEQ ID NO 11
<211> LENGTH: 30
<212> TYPE: DNA
<213> ORGANISM: Artificial
<220> FEATURE:
<223> OTHER INFORMATION: completely synthesized

<400> SEQUENCE: 11
tacgctccca gtgtgatcac caaagcttac                                      30

<210> SEQ ID NO 12
<211> LENGTH: 30
<212> TYPE: DNA
<213> ORGANISM: Artificial
<220> FEATURE:
<223> OTHER INFORMATION: completely synthesized

<400> SEQUENCE: 12
gtaagctttg gtgatcacac tgggagcgta                                      30

<210> SEQ ID NO 13
<211> LENGTH: 30
<212> TYPE: DNA
<213> ORGANISM: Artificial
<220> FEATURE:
<223> OTHER INFORMATION: completely synthesized

<400> SEQUENCE: 13
agactgaact accggcggtt gcactactaa                                      30

<210> SEQ ID NO 14
<211> LENGTH: 30
<212> TYPE: DNA
<213> ORGANISM: Artificial
<220> FEATURE:
<223> OTHER INFORMATION: completely synthesized

<400> SEQUENCE: 14
ttagtagtgc aaccgccggt agttcagtct                                      30

<210> SEQ ID NO 15
<211> LENGTH: 30
<212> TYPE: DNA
<213> ORGANISM: Artificial
<220> FEATURE:
<223> OTHER INFORMATION: completely synthesized

<400> SEQUENCE: 15
gccaaacacg cccaatcact gttacatgtc                                      30

<210> SEQ ID NO 16
<211> LENGTH: 30
<212> TYPE: DNA
<213> ORGANISM: Artificial
<220> FEATURE:
<223> OTHER INFORMATION: completely synthesized

<400> SEQUENCE: 16
```

```
gacatgtaac agtgattggg cgtgtttggc                                30
```

<210> SEQ ID NO 17
<211> LENGTH: 30
<212> TYPE: DNA
<213> ORGANISM: Artificial
<220> FEATURE:
<223> OTHER INFORMATION: completely synthesized

<400> SEQUENCE: 17

```
gcttgacgtc taccaccgtg aacataagga                                30
```

<210> SEQ ID NO 18
<211> LENGTH: 30
<212> TYPE: DNA
<213> ORGANISM: Artificial
<220> FEATURE:
<223> OTHER INFORMATION: completely synthesized

<400> SEQUENCE: 18

```
tccttatgtt cacggtggta gacgtcaagc                                30
```

<210> SEQ ID NO 19
<211> LENGTH: 30
<212> TYPE: DNA
<213> ORGANISM: Artificial
<220> FEATURE:
<223> OTHER INFORMATION: completely synthesized

<400> SEQUENCE: 19

```
tcgccaacgt agctgtgcta cagttgattc                                30
```

<210> SEQ ID NO 20
<211> LENGTH: 30
<212> TYPE: DNA
<213> ORGANISM: Artificial
<220> FEATURE:
<223> OTHER INFORMATION: completely synthesized

<400> SEQUENCE: 20

```
gaatcaactg tagcacagct acgttggcga                                30
```

<210> SEQ ID NO 21
<211> LENGTH: 30
<212> TYPE: DNA
<213> ORGANISM: Artificial
<220> FEATURE:
<223> OTHER INFORMATION: completely synthesized

<400> SEQUENCE: 21

```
gcagcggcta aaccttgaga tcgaatggaa                                30
```

<210> SEQ ID NO 22
<211> LENGTH: 30
<212> TYPE: DNA
<213> ORGANISM: Artificial
<220> FEATURE:
<223> OTHER INFORMATION: completely synthesized

<400> SEQUENCE: 22

```
ttccattcga tctcaaggtt tagccgctgc                                30
```

<210> SEQ ID NO 23
<211> LENGTH: 30
<212> TYPE: DNA

```
<213> ORGANISM: Artificial
<220> FEATURE:
<223> OTHER INFORMATION: completely synthesized

<400> SEQUENCE: 23
tgcgatatac tccatgcctc tcttggcgga                              30

<210> SEQ ID NO 24
<211> LENGTH: 30
<212> TYPE: DNA
<213> ORGANISM: Artificial
<220> FEATURE:
<223> OTHER INFORMATION: completely synthesized

<400> SEQUENCE: 24
tccgccaaga gaggcatgga gtatatcgca                              30
```